US011111261B2

(12) United States Patent
Christensen et al.

(10) Patent No.: US 11,111,261 B2
(45) Date of Patent: Sep. 7, 2021

(54) IRON COMPLEX COMPOUNDS FOR THERAPEUTIC USE

(71) Applicant: Pharmacosmos Holding A/S, Holbæk (DK)

(72) Inventors: Tobias S. Christensen, Roskilde (DK); Hans B. Andreasen, Holbæk (DK)

(73) Assignee: Pharmacosmos Holding A/S, Holbaek (DK)

( * ) Notice: Subject to any disclaimer, the term of this patent is extended or adjusted under 35 U.S.C. 154(b) by 0 days.

(21) Appl. No.: 16/274,552

(22) Filed: Feb. 13, 2019

(65) Prior Publication Data

US 2019/0177353 A1    Jun. 13, 2019

Related U.S. Application Data

(63) Continuation of application No. PCT/EP2018/074293, filed on Sep. 10, 2018.

(30) Foreign Application Priority Data

Sep. 11, 2017 (EP) .................................... 17190302

(51) Int. Cl.
| | | |
|---|---|---|
| *C07H 3/06* | (2006.01) | |
| *A61K 33/26* | (2006.01) | |
| *C07H 23/00* | (2006.01) | |
| *C07H 1/00* | (2006.01) | |
| *A61P 7/06* | (2006.01) | |

(52) U.S. Cl.
CPC .............. *C07H 3/06* (2013.01); *A61K 33/26* (2013.01); *C07H 1/00* (2013.01); *C07H 23/00* (2013.01); *A61P 7/06* (2018.01)

(58) Field of Classification Search
None
See application file for complete search history.

(56) References Cited

U.S. PATENT DOCUMENTS

| | | |
|---|---|---|
| 3,639,588 A | 2/1972 | Alsop et al. |
| 3,906,077 A | 9/1975 | Rado et al. |
| 4,056,386 A | 11/1977 | McEwan et al. |
| 6,291,440 B1 | 9/2001 | Andreasen et al. |
| 6,977,249 B1 | 12/2005 | Andreasen et al. |
| 8,815,301 B2 * | 8/2014 | Andreasen ............. A61K 47/26 424/647 |
| 8,926,947 B2 | 1/2015 | Groman et al. |
| 9,439,969 B2 | 9/2016 | Andreasen |
| 2012/0010166 A1 | 1/2012 | Andreasen |
| 2014/0296509 A1 | 10/2014 | Groman et al. |
| 2014/0303364 A1 | 10/2014 | Andreasen |
| 2014/0364598 A1 | 12/2014 | Andreasen |
| 2016/0333118 A1 | 11/2016 | Andreasen |
| 2018/0042960 A1 | 2/2018 | Thomsen et al. |

FOREIGN PATENT DOCUMENTS

| | | | |
|---|---|---|---|
| CA | 2318823 A1 | 9/1999 | |
| EP | 1554315 B1 | 4/2011 | |
| EP | 2913054 A1 | 9/2015 | |
| FR | 0654013 * | 9/1996 | ............. C01G 49/10 |
| WO | 1999048533 A1 | 3/1999 | |
| WO | 9948533 A1 | 9/1999 | |
| WO | 2008096130 A1 | 2/2008 | |
| WO | 2010108493 A1 | 3/2009 | |
| WO | 2010108493 A1 | 9/2010 | |
| WO | 2016066172 A1 | 10/2015 | |
| WO | 2016206600 A1 | 6/2016 | |
| WO | 2016206699 A1 | 6/2016 | |

OTHER PUBLICATIONS

Gordeuk et al. Blood, vol. 67, No. 3 Mar. 1986, 745-752.*
Farius et al. Revista Braileira de Hematologia e Hemoterapia, vol. 31, 2009.*
International Search Report for Int'l Appl. No. PCT/EP2018/074293, filed Sep. 10, 2018, and dated Oct. 18, 2018.
Kernkamp et al. "Preventing iron-deficiency anemia in baby pigs." Journal of Animal Science Aug. 1962;21(3):527-32.
Zimmerman, D. R., et al. "Injectable iron-dextran and several oral iron treatments for the prevention of iron-deficiency anemia of baby pigs." Journal of Animal Science, Nov. 1959;18(4):1409-15.
Cain et al. "Preparation of Pure Iron and Iron-carbon Alloys." Industrial & Engineering Chemistry. Mar. 1916;8(3):217-24.
Mostad et al. "Electrowinning of iron from sulphate solutions." Hydrometallurgy. Feb. 2008;90(2-4):213-20.
Jahn et al. "A comparative study of the physicochemical properties of iron isomaltoside 1000 (Monofer®), a new intravenous iron preparation and its clinical implications." European journal of pharmaceutics and blophamtaceutics. Aug. 2011;78(3):480-91.
Radke et al. "Elemental impurities in injectable iron products for swine." Journal of Swine Health and Production. May 1, 2018;26(3):142-5.
"Iron Dextran Injection." British Pharmacopoeia. 2017. vol. III.
International Conference on Harmonisation of Technical Requirements for Registration of Pharmaceuticals for Human use. "Guideline for Elemental Impurities Q3D." (2014).
US Department of Health and Human Services. "Q3D Elemental Impurities Guidance for Industry." (2015).

(Continued)

*Primary Examiner* — Clinton A Brooks
(74) *Attorney, Agent, or Firm* — Robin L. Teskin; Baker, Donelson, Bearman, Caldwell & Berkowitz PC

(57) ABSTRACT

The present invention relates to iron complex compounds for therapeutic use which are low in arsenic, chromium, lead, cadmium, mercury and/or aluminum, compositions thereof and processes for preparing said iron complex compounds.

25 Claims, No Drawings

(56) References Cited

OTHER PUBLICATIONS

Lanphear et al. "Low-level lead exposure and mortality in US adults: a population-based cohort study." The Lancet Public Health. Apr. 1, 2018;3(4):e177-84.

* cited by examiner

IRON COMPLEX COMPOUNDS FOR THERAPEUTIC USE

CROSS REFERENCE TO RELATED APPLICATIONS

This application is a Continuation of International Patent Appl. No. PCT/EP2018/074293, filed Sep. 10, 2018, which claims priority to International Patent Appl. No. EP 17190302.4, filed Sep. 11, 2017, the disclosures of each of which are hereby incorporated by reference in their entireties.

FIELD OF THE INVENTION

The present invention relates to iron complex compounds for therapeutic use which are low in arsenic, lead, chromium, mercury, cadmium and/or aluminum, compositions thereof and processes for preparing said iron complex compounds.

BACKGROUND OF THE INVENTION

The risks of iron deficiency and iron deficiency anemia are highly relevant for the health of humans and livestock worldwide.

Iron deficiency is associated with a number of common conditions including pregnancy and lactation, childhood development, gastrointestinal bleeding, inflammatory bowel disease, congestive heart failure, restless leg syndrome, parasitic infections, chronic ingestion of certain agents, impaired kidney function and numerous others. Iron products are commonly used to treat or prevent iron deficiency and anemia associated therewith in humans.

Prevention and treatment of iron deficiency is also an important aspect in livestock farming. For example, the use of injectable iron for prevention of iron deficiency anemia is nearly an industry standard in swine production throughout the world. Since initial reports in the mid-twentieth century detailed a piglet's need for supplemental iron, 200 mg doses of injectable iron have routinely been given to every pig as per product label directions (Kernkamp et al., J Anim Sci. 1962, 21:527-532; Ullrey et al., J Anim Sci. 1959, 18:256-263; Zimmerman et al., J Anim Sci. 1959, 18:1409-1415). The administration of iron products to livestock is thus an established and often necessary practice in livestock farming.

Various forms of iron products for use in the treatment or prevention of iron deficiency and anemia associated therewith have been described. See, for example, WO 2016/206600 A1, WO 2016/066172 A1, WO 2010/108493 A1, WO 99/48533 A1, U.S. Pat. No. 6,977,249 B1, EP 1 554 315 B1, U.S. Pat. No. 8,926,947 B2 and WO 2008/096130 A1, to name but a few.

It is an object of the present invention to provide iron products which are safe for administration to humans and to livestock as well as for human consumers of food produced from livestock.

SUMMARY OF THE INVENTION

The inventors found that conventional iron products, in particular iron products for veterinary use, often contain relatively high amounts of non-iron metal impurities, such as arsenic, chromium, lead, mercury, cadmium or aluminum, which can be harmful to the health of humans and/or non-human animals. Accumulation of such impurities over the food chain up to human consumers of livestock products may exacerbate this health risk. The inventors therefore devised a novel process for preparing iron complex compounds which are low in impurities such as arsenic, chromium, lead, mercury, cadmium and/or aluminum.

In one aspect, the present invention thus provides a process for preparing an iron complex compound comprising the steps of
(i) providing an iron preparation comprising iron in a form selected from a water-soluble iron salt, an iron hydroxide, an iron oxide-hydroxide and a mixture of two or more thereof, wherein
the amount of arsenic in the iron preparation does not exceed 4.5 µg per g of iron, and
the amount of lead in the iron preparation does not exceed 1.5 µg per g of iron; and
(ii) contacting the iron preparation with a ligand in the presence of water so as to form the iron complex compound.

In a further aspect, the present invention provides an iron complex compound obtained by the process of the invention.

In a further aspect, the present invention provides an iron complex compound, wherein
the amount of arsenic in the iron preparation does not exceed 4.5 µg per g of iron, and
the amount of lead in the iron preparation does not exceed 1.5 µg per g of iron.

In a further aspect, the present invention provides an iron complex compound, wherein the amount of aluminum in the iron complex compound does not exceed 200 µg per g iron.

In a further aspect, the present invention provides a composition comprising the iron complex compound of the invention and a pharmaceutically acceptable carrier.

In a further aspect, the present invention provides an iron complex compound or composition of the invention for therapeutic use.

In a related aspect, the present invention provides an iron complex compound or composition of the invention for use in treatment or prophylaxis of iron-deficiency in a subject.

The present invention also relates to the use of an iron complex compound or composition of the invention in the manufacture of a medicament for treatment or prophylaxis of iron-deficiency in a subject. The present invention also relates a method for treatment or prophylaxis of iron-deficiency in a subject by administering an effective amount of an iron complex compound or composition of the invention to the subject.

DETAILED DESCRIPTION OF THE INVENTION

Unless further specified, the term "iron complex compound" as used herein refers to any complex of iron ions or iron particles comprising $Fe^{3+}$ and/or $Fe^{2+}$ and a ligand.

Expediently, the ligands and salts used in the iron complex compounds of the invention as well as the carriers and other ingredients of the compositions thereof are physiologically acceptable. The term "physiologically acceptable" as used herein, means that the ligand, salt, carrier or other ingredient does not cause acute toxicity when a therapeutically effective amount of the iron complex compound or the composition comprising the ligand, salt, carrier or other ingredient is administered to a subject.

Unless not further specified, the term "carbohydrate" as used herein includes carbohydrates which are reduced, oxidized, derivatized or a combination thereof as described herein. In particular, carbohydrates can be derivatized, for example, by the formation of ethers, amides, esters and amines with the hydroxyl groups of the carbohydrates or by the conversion of aldehyde groups of the carbohydrates to glycolic groups so as to form heptonic acids, for example dextran glucoheptonic acids or dextrin glucoheptonic acids, using a process as described, e.g., in U.S. Pat. No. 3,639,588. The term "carbohydrate" as used herein is thus not limited to compounds having the empirical formula $C_m(H_2O)_n$, wherein m and n are integers which may be the same or different from each other.

Carbohydrates which may be used as ligands in iron carbohydrate complex compounds of the present invention include, for example, monosaccharides; disaccharides, e.g. sucrose and maltose; oligosaccharides and polysaccharides, e.g. maltodextrin, polyglucose, dextran, polymaltose and oligomaltose, polyisomaltose and oligoisomaltose; sugar alcohols, e.g. sorbitol and mannitol; sugar acids and salts thereof, e.g. gluconic acid, gluconate, dextran glucoheptonic acid, dextrin glucoheptonic acid, dextran glucoheptonate and dextrin glucoheptonate, as well as reduced and/or oxidized and/or derivatized variants thereof, e.g. carboxymaltose, polyglucose sorbitol carboxymethyl ether, hydrogenated dextran, oxidized dextran, carboxyalkylated oligo- and polysaccharides, oxidized oligo- and polysaccharides, hydrogenated dextrin, oxidized dextrin, hydrogenated polymaltose, hydrogenated oligomaltose, hydrogenated polyisomaltose, hydrogenated oligoisomaltose, hydrogenated oligomaltose, hydroxyethyl starch or a mixture of two or more thereof. In preferred embodiments, the carbohydrate is carboxymaltose, polyglucose sorbitol carboxymethyl ether, mannitol, dextran, hydrogenated dextran, sucrose, gluconate, dextrin, hydrogenated oligoisomaltose (oligoisomaltoside) or a mixture of two or more thereof.

The term "oligosaccharide" as used herein refers to a carbohydrate, or a reduced and/or oxidized and/or derivatized variant thereof, having a small number, typically 3-10, monosaccharide units, or to a mixture of two or more carbohydrates, or reduced and/or oxidized and/or derivatized variants thereof, wherein the majority (e.g., at least 60%, at least 70%, at least 80% or more) of the molecules have a small number, typically 3-10, monosaccharide units.

The term "monomer saccharide" as used herein refers to a monosaccharide or a reduced and/or oxidized and/or derivatized variant thereof, or to a mixture of two or more monosaccharides and/or variants thereof.

The term "dimer saccharide" as used herein refers to a carbohydrate having two monosaccharide units (such as a disaccharide) or a reduced and/or oxidized and/or derivatized variant thereof, or to a mixture of two or more carbohydrates, or reduced and/or oxidized and/or derivatized variants thereof, wherein the majority (e.g., at least 60%, at least 70%, at least 80% or more) of the molecules have two monosaccharide units.

Sugar alcohols are mono- or disaccharide derivatives wherein the aldehyde group is converted to a hydroxyl group.

Sugar acids are monosaccharide derivatives which carry a carboxyl group. The carboxyl group can be obtained by, for example, oxidizing the aldehyde group of an aldose so as to form an aldonic acid, oxidizing the 1-hydroxyl group of a 2-ketose so as to form an α-ketoacid (ulosonic acid), oxidizing the terminal hydroxyl group of an aldose or ketose so as to obtain an uronic acid, or oxidizing both ends of an aldose so as to obtain an aldaric acid.

In step (i) of the process of the invention, an iron preparation is provided that is low in arsenic and lead, and optionally is also low in chromium, mercury, cadmium and/or aluminum.

The amounts of said non-iron metals are indicated herein relative to the amount of iron in the iron preparation or iron complex compound. Metals such as iron, arsenic, chromium, lead, mercury, cadmium and aluminum exist in different forms (elemental form, salts, complex compounds). The amounts of iron and non-iron metals such as arsenic, chromium, lead, mercury, cadmium and aluminum indicated herein refer to the total amount of the respective metal, regardless in which form it is present.

The amounts of non-iron metals are preferably determined using Inductively Coupled Plasma (ICP) methods such as Inductively coupled plasma mass spectrometry (ICP-MS). Examples of devices that can be used for this purpose include, but are not limited to, 8800 Triple Quadrupole ICP-MS (Agilent Technologies) and ICP-MS devices of the iCAP™ Q series (Thermo Fisher Scientific). Methods such as Atomic Absorption Spectroscopy (AAS) which have relatively high measurement limits and/or are sensitive to interference with iron are generally not recommended.

Unless specified differently, the term "about" as used herein in the context of a particular value indicates that the value can vary by up to 20%, in particular up to 10% and more particularly up to 5%, e.g. up to 1%.

In the iron preparation used in the process of the invention,
  the amount of arsenic does not exceed 4.5 µg per g iron, for example does not exceed 3.0 µg per g iron, 2.5 µg per g iron or 2.0 µg per g iron, and in particular does not exceed 1.5 µg per g iron, for example does not exceed 1.0 µg per g iron, 0.8 µg per g iron, 0.5 µg per g iron or 0.3 µg per g iron; and
  the amount of lead does not exceed 1.5 µg per g iron, 1.3 µg per g iron, 1.0 µg per g iron or 0.7 µg per g iron, and in particular does not exceed 0.5 µg per g iron, for example does not exceed 0.4 µg per g iron or 0.2 µg per g iron; and
  optionally, the amount of cadmium does not exceed 0.6 µg per g iron, for example does not exceed 0.5 µg per g iron, and in particular does not exceed 0.4 µg per g iron, for example does not exceed 0.3 µg per g iron or 0.2 µg per g iron; and
  optionally, the amount of mercury does not exceed 0.9 µg per g iron, for example does not exceed 0.7 µg per g iron or 0.5 µg per g iron, and in particular does not exceed 0.3 µg per g iron, for example does not exceed 0.2 µg per g iron or 0.10 µg per g iron; and
  optionally, the amount of chromium does not exceed 330 µg per g iron, for example does not exceed 250 µg per g iron or 170 µg per g iron, and in particular does not exceed 100 µg per g iron, example does not exceed 75 µg per g iron, 50 µg per g iron or 20 µg per g iron; and
  optionally, the amount of aluminum does not exceed 200 µg per g iron, for example does not exceed 150 µg per g iron, 100 µg per g iron or 50 µg per g iron, and in particular does not exceed 25 µg per g iron, for example does not exceed 20 µg per g iron or 15 µg per g iron.

The iron preparation used in the process of the invention comprises iron in a form selected from a water-soluble iron salt, an iron hydroxide and an iron oxide-hydroxide. The iron preparation may contain a mixture of two or more of these iron forms.

In a particular embodiment, the iron preparation comprises a water-soluble iron salt, for example an iron bromide, sulfate or chloride, in particular ferric chloride ($FeCl_3$), ferrous chloride ($FeCl_2$) or a mixture thereof. Expediently, the water-soluble iron salt is a physiological acceptable salt.

In a further particular embodiment, the iron preparation comprises iron hydroxide, for example ferric hydroxide ($Fe(OH)_3$), ferrous hydroxide ($Fe(OH)_2$) or a mixture thereof.

In a further particular embodiment, the iron preparation comprises iron oxide-hydroxide. Iron oxide-hydroxides may also be termed iron oxy-hydroxides. Iron oxide-hydroxides are compounds which consist of one or more than one iron ion, one or more than one oxo group, and one or more than one hydroxyl group. Particular iron oxide-hydroxides include, e.g., ferric oxide-hydroxides which occur in anhydrous ($FeO(OH)$) forms and hydrated ($FeO(OH).nH_2O$) forms such as, e.g., ferric oxide-hydroxide monohydrate ($FeO(OH).H_2O$). Iron oxide-hydroxides can be prepared for example from aqueous iron(III) salt solutions by hydrolysis and precipitation as described, e.g., in Rómpp lexicon Chemie, 10. Auflage, 1997. Iron oxide-hydroxides can be present in different polymorphic forms. For example, polymorphs of $FeO(OH)$ include $\alpha$-$FeO(OH)$ (goethite), $\beta$-$FeO(OH)$ (akagneite), $\gamma$-$FeO(OH)$ (lepidocrocite) and $\delta$-$FeO(OH)$ (feroxyhyte).

The iron preparation used in the process of the present invention, i.e. an iron preparation that is low in non-iron metal impurities as required by the invention, can be obtained (a) from iron pentacarbonyl; or
(b) by recrystallization of an iron salt from an aqueous solution thereof; or
(c) by extracting an aqueous iron salt solution with an organic solvent; or
(d) from iron precipitated at an anode during electrolysis of an aqueous iron salt solution; or
(e) by contacting an aqueous iron salt solution with a base so as to form a precipitate of iron hydroxide and separating the precipitate from the liquid by filtration or centrifugation; or
(f) by distillation of ferric chloride from a mixture comprising ferric chloride and non-volatile impurities.

According to a preferred embodiment, the iron preparation is obtained by a process wherein an aqueous iron salt solution (e.g., an aqueous iron salt solution obtained during the processing of an iron-containing nickel ore for nickel production) is extracted with an organic solvent.

According to a particularly preferred embodiment, the iron preparation used in the process of the invention is prepared from iron pentacarbonyl.

The generation of an iron preparation as described herein:
(a) from iron pentacarbonyl, or
(b) by recrystallization of an iron salt from an aqueous solution thereof, or
(c) by extracting an aqueous iron salt solution with an organic solvent, or
(d) from iron precipitated at an anode during electrolysis of an aqueous iron salt solution, or
(e) by contacting an aqueous iron salt solution with a base so as to form a precipitate of iron hydroxide and separating the precipitate from the liquid by filtration or centrifugation, or
(f) by distillation of ferric chloride from a mixture comprising ferric chloride and non-volatile impurities can, but is not required to, be a step of the process of the present invention.

Methods for preparing a water-soluble iron salt, iron hydroxide or iron oxide-hydroxide from iron pentacarbonyl are known in the art. For example, in a first step, iron pentacarbonyl can be decomposed to form iron (so-called carbonyl iron) at an elevated temperature (e.g. 200° C. or more), optionally in the presence of a catalyst such as $H_2$, NO, $PF_3$, $PH_3$, $NH_3$ and/or $I_2$, as described for example in U.S. Pat. No. 4,056,386. The iron can be reacted with (preferably an excess of) hydrochloric acid so as to obtain $FeCl_2$. $FeCl_2$ can be reacted with hydrochloric acid and (preferably a slight deficit of) sodium chlorate so as to obtain $FeCl_3$. $FeCl_2$ can be reacted with hydrochloric acid and oxidized using, for example, hydrogen peroxide so as to form $FeCl_3$. This reaction can be used to oxidize $FeCl_2$ remaining from the reaction with hydrochloric acid and sodium chlorate so as to achieve a more complete conversion of $FeCl_2$ to $FeCl_3$. Also chlorine ($Cl_2$; gas) can be used as oxidation agent.

Carbonyl iron can be prepared, for example, by directing carbon monoxide onto hot iron (e.g., as hot as about 200° C.), preferably under high pressure (e.g., as high as 15-20 MPa). Such preparation of carbonyl iron is described, for example, in French patent application no. 607.134 of Badische Anilin- & Soda-Fabrik published on Jun. 26, 1926.

Methods for preparing an iron preparation as described herein by recrystallization of an iron salt preparation from an aqueous solution thereof are known in the art. To this end, an aqueous solution of a water-soluble iron salt preparation is provided, the iron salt (e.g., ferric nitrate) is recrystallized from the solution (e.g., by reducing the temperature of the solution), the iron salt crystals are separated from the liquid, are dissolved so as to form an aqueous solution thereof and then again subjected to recrystallization and separation. The steps of dissolution, recrystallization and separation can be repeated for one or several more times so as to increase the purity, and in particular reduce the amount of non-iron metal impurities, of the iron salt preparation. According to a particular example, ferric nitrate is recrystallized from an aqueous solution thereof containing nitric acid. Specifically, ferric nitrate is dissolved in about 55-65% aqueous nitric acid at about 50-60° C. The solution is cooled to about 15° C. or lower temperature, where crystalline ferric nitrate precipitate is formed and can be separated from the liquid. Said steps of dissolution, recrystallization and separation can be repeated for one or several more times.

Methods for preparing an iron preparation as described herein by extracting an aqueous iron salt solution with an organic solvent are known in the art. To this end, an aqueous ferric chloride solution can be treated with an organic solvent so as to selectively dissolve the ferric chloride in the organic solvent (extraction), then the selectively dissolved ferric chloride can be recovered by stripping the organic solvent from the ferric chloride.

Exemplary organic solvents include alcohols having about 4-20 carbon atoms, in particular alcohols having 6-10 carbon atoms, such as n-octanol, and organic solutions of amine salts such as tri-n-laurylamine hydrochloride in toluene. The presence of hydrochloric acid in the aqueous ferric chloride solution can improve extraction efficiency. It is advantageous to increase the concentration of ferric chloride in the aqueous starting solution by partial evaporation before adding the organic solvent, in particular to a concentration in the range of 280-850 g/l ferric chloride. The purification cycle of evaporation and solvent extraction can be repeated until the desired purity of the ferric chloride preparation is obtained. Aqueous solutions of ferrous chloride can also be purified if the ferrous chloride is first converted to ferric chloride by oxidation with chlorine. Specific methods for extraction of iron salts with organic solvents are described, e.g., in CA 2318 823 A1 and Müller et al. ("Liquid-liquid extraction of ferric chloride by tri-n-laurylamine hydrochloride", EUR 2245.e, Euratom report, Transplutonium Elements Program, Euratom Contract No. 003-61-2 TPUB, Presses Academiques Europeennes, Brussels, 1965).

Methods for electrolysis of aqueous iron salt solutions wherein iron is precipitated at an anode are known in the art. See, for example, Cain et al. ("Preparation of pure iron and iron-carbon alloy" in Bulletin of the Bureau of Standards, Vol. 13, 1916) and Mostad et al. (Hydrometallurgy, 2008, 90, 213-220). Suitable iron solutions for electrolysis include iron chloride solutions, iron sulfate solutions and solutions containing both iron chloride and iron sulfate. The solution is typically neutral or acidic.

An iron preparation as described herein can further be obtained by contacting an aqueous iron salt solution with a base so as to form a precipitate of iron hydroxide and separating the precipitate from the liquid by filtration or centrifugation. Suitable bases for precipitation of iron hydroxides include sodium hydroxide or sodium carbonate. Alternatively, sodium bicarbonate can be used. Methods for separating such precipitate from the remaining solution by filtration or centrifugation are known in the art.

An iron preparation that is low in non-iron metal impurities, such as the iron preparation used in the process of the invention, can also be prepared by distillation of a mixture comprising ferric chloride and non-volatile impurities. For distillation, the mixture is subjected to a temperature and a pressure which are chosen such that at the selected pressure and temperature the mixture is at about its boiling point. At those conditions, the mixture separates into a vapor phase and a slurry of non-volatile impurities in liquid ferric chloride. The vapor is substantially pure ferric chloride that can be recovered by separating the vapor from the slurry. According to particular embodiments, a temperature at about the boiling point of the mixture means a temperature that is within 10° C. of said boiling point and preferably is at said boiling point. Distillation can be performed, e.g., at a temperature in the range of from 300° C. to 700° C. and a pressure in the range of from 0.1 to 5.1 MPa, preferably in the range of from 0.2 to 0.4 MPa, wherein at the selected pressure and temperature the mixture is at about its boiling point.

During distillation, settlement of non-volatile solids in the slurry can be prevented by agitating the slurry mechanically (e.g., by paddle stirrer or the like) or, preferably, by bubbling a gas (e.g., nitrogen, helium, chlorine or a mixture thereof) through the slurry.

After separation of the ferric chloride vapor, the remaining slurry can be recycled by heating the slurry so as to vaporize ferric chloride, separating and cooling the ferric chloride containing vapor and reintroducing it to the distillation process. Preferably, the recycling of the slurry is performed such that the amount of solids present in the slurry during distillation is below about 20 wt-%, in particular below about 12 wt-%.

The mixture comprising ferric chloride and non-volatile impurities that is introduced into the distillation process can be obtained, for example, by chlorinating iron-containing ore (e.g., a titaniferous ore such as ilmenite) so as to produce a gaseous mixture comprising ferric chloride and non-volatile impurities and cooling the gas so as to precipitate a solid mixture of ferric chloride and non-volatile impurities. Said solid mixture can then be introduced into the distillation process. Prior to separating the solid mixture of ferric chloride and non-volatile impurities from the gaseous mixture, the gaseous mixture can optionally be subjected to a temperature above the dew-point of ferric chloride so as to remove non-volatile impurities which are no longer gaseous at this temperature. The thus pre-purified gaseous mixture can then be cooled so as to precipitate a solid mixture of ferric chloride and non-volatile impurities that can be introduced into the distillation process. See, for example, U.S. Pat. No. 3,906,077.

Different methods for preparing and purifying iron preparations can be combined so as to increase the purity of the iron preparation even further. For example, iron prepared by electrolysis of an aqueous iron salt solution can be converted into a water-soluble iron salt that is then subjected to one or more cycles of (1) dissolution so as to form an aqueous solution of the iron salt,
(2) recrystallization of the iron salt from the aqueous solution and
(3) separation of the recrystallized iron salt from the remaining solution.

Iron complex compounds of the invention can be prepared by contacting an iron preparation that is low in arsenic and lead, and optionally is also low in chromium, mercury, cadmium and/or aluminum as described herein with a ligand in the presence of water. This represents step (ii) of the process for preparing an iron complex compound of the invention. Iron preparations comprising iron in the form of an iron hydroxide and/or iron oxide-hydroxide can be used directly for this step. For example, a precipitate of iron hydroxide (e.g., ferric hydroxide) and/or iron oxide-hydroxide in an aqueous solution is contacted with a ligand (e.g., a carbohydrate preparation), followed by heating and raising the pH so as to form an iron complex compound (e.g., an iron complex compound comprising FeO(OH) cores). Alternatively, the iron hydroxide and/or iron oxide-hydroxide of the iron preparation is converted into a water-soluble iron salt as described herein by contacting the iron preparation with an acid. Expediently this conversion is performed in an aqueous solution comprising the reactants (iron hydroxide and/or iron oxide-hydroxide and acid). The choice of the acid depends on the iron salt to be produced. For example, iron chloride can be prepared by reacting the iron hydroxide and/or iron oxide-hydroxide of an iron preparation with hydrochloric acid. The reagents which, in addition to the iron preparation, are used in step (ii) of the process of the invention for preparing the iron complex compound are expediently substantially free of non-iron impurities such as arsenic, chromium, lead, mercury, cadmium and/or aluminum.

According to one group of embodiments, the iron complex compound is an iron carbohydrate complex compound, i.e. the ligand in the iron complex compound is a carbohydrate.

Preferably, the content of reducing aldehyde groups in the carbohydrate is at least partially reduced. This can be achieved by hydrogenation, oxidation or a combination thereof. Iron carbohydrate complex compounds comprising carbohydrates which are hydrogenated and/or oxidized can be prepared as described, for example, in U.S. Pat. No. 8,929,947 B2, EP 1 554 315 B1, U.S. Pat. No. 6,977,249 B1, WO 2010/108493 A1 or WO 99/48533 A1. The amount of reducing carbohydrate can be determined using Somogyi's reagent.

Specifically, the aldehyde groups can be converted into hydroxyl groups by hydrogenation, for example by reacting the carbohydrate with a reducing agent, such as sodium borohydride in aqueous solution, or with hydrogen in the presence of a hydrogenation catalyst, such as Pt or Pd.

Alternatively or additionally to hydrogenation, the aldehyde groups can be oxidized, for example by oxidation of the carbohydrate using an aqueous hypochlorite solution at a pH within the alkaline range, e.g. within the range of from pH 8 to pH 12, in particular from pH 9 to pH 11. Suitable hypochlorites include, for example, alkali metal hypochlorites such as sodium hypochlorite. The aqueous hypochlorite solution can have a concentration of, for example, at least 13 wt-%, in particular in the range of from 13 to 16 wt-%, calculated as active chlorine. The oxidation reaction can be performed at temperatures in the range of, for example, from 15 to 40° C., preferably from 25 to 35° C. Reaction times are, for example, in the range of from 10 min to 4 hours, such as from 1 to 1.5 hours. The addition of catalytic amounts of bromine ions, e.g. in the form of alkali metal bromides such as sodium bromide, can further the oxidation reaction but is not mandatory.

The aldehyde groups of the carbohydrate can be converted by both hydrogenation and oxidation. This can be achieved, for example, in that the carbohydrate is first hydrogenated to convert part of the aldehyde groups into hydroxyl groups, and then substantially all of the remaining aldehyde groups are oxidized to carboxyl groups. Where the carbohydrate is a polysaccharide such as dextran, the average molecular weight of the iron carbohydrate complex formed therewith can be influenced by adjusting the ration of hydrogenated aldehyde groups to oxidized aldehyde groups. To obtain a stable product, the amount of reducing groups in the carbohydrate (e.g. dextran) before oxidation does not exceed 15 wt-%.

The carbohydrates, including reduced and/or oxidized carbohydrates, can be derivatized by formation of, for example, ethers, amides, esters and amines with the hydroxyl groups of the carbohydrates. In a particular embodiment, the carbohydrate is derivatized by formation of carboxyalkyl ether, in particular carboxymethyl ether, with a hydroxyl group of the carbohydrate. The use of carboxymethylated carbohydrate in a product such as an iron carbohydrate complex compound of the invention may reduce the toxicity of the product when administered parenterally to a subject compared to a product comprising a corresponding non-carboxylated carbohydrate.

Iron carbohydrate complex compounds of the present invention include, for example, iron carboxymaltose, iron polyglucose sorbitol carboxymethyl ether complex, iron mannitol complex, iron dextran, iron hydrogenated dextran, iron oxidized dextran, iron carboxyalkylated reduced oligo- and polysaccharides, iron sucrose, iron gluconate, iron dextrin, iron hydrogenated dextrin, iron oxidized dextrin, iron polymaltose, iron hydrogenated polymaltose, iron oligomaltose, hydrogenated iron oligomaltose, iron polyisomaltose, iron hydrogenated polyisomaltose, iron hydrogenated oligosaccharides such as iron hydrogenated oligoisomaltose, iron hydroxyethyl starch, iron sorbitol, iron dextran glucoheptonic acid (e.g., gleptoferron) and a mixture of two or more thereof. According to particular embodiments, the iron carbohydrate complex compound of the present invention is selected from iron carboxymaltose, iron polyglucose sorbitol carboxymethyl ether complex, iron mannitol complex, iron dextran, iron hydrogenated dextran, iron sucrose, iron gluconate, iron dextrin, iron hydrogenated oligoisomaltose and a mixture of two or more thereof.

The carbohydrate in iron carbohydrate complex compounds of the invention typically has a weight average molecular weight ($M_W$) of from 500 to 80,000 Da, such as from 800 to 40,000 Da or from 800 to 10,000 Da and in particular from 800 to 3,000 Da.

The apparent molecular weight ($M_p$) of the iron carbohydrate complex compounds of the invention is typically in the range of from 800 to 800,000 Da, such as from 10,000 to 500,000 Da or from 20,000 to 400,000 Da or from 50,000 to 300,000 Da and in particular from 90,000 to 200,000 Da. The apparent molecular weight $M_p$ can be determined by gel-permeation chromatography using, e.g., dextran standards. See, for example, the method described in Jahn et al., Eur J Pharm Biopharm 2011, 78, 480-491.

The amount of dimer in carbohydrate preparations which are (optionally reduced and/or oxidized and/or derivatized) oligosaccharide or polysaccharide preparations was found to be a key factor with regard to the stability of the iron carbohydrate complex compounds prepared therefrom. See WO 2010/108493 A1. In iron carbohydrate complex compounds of the invention where the carbohydrate is an (optionally reduced and/or oxidized and/or derivatized) oligosaccharide or polysaccharide preparation, the content of dimer saccharides in said preparation is therefore preferably 2.9 wt-% or less, in particular 2.5 wt-% or less, and especially 2.3 wt-% or less, based on the total weight of the carbohydrate. It is also preferred that the content of monomer saccharide in the carbohydrate preparation is 0.5 wt-% or less, based on the total weight of the carbohydrate. This reduces the risk of toxic effects caused by free iron ions released from compounds of monomer and iron, especially when present in preparations for parenteral administration. Low amounts of dimer saccharides and/or monomer saccharides as indicated above can be obtained, e.g., by removing said smaller saccharide molecules from a carbohydrate preparation by a purification method such as membrane filtration, for examples using membranes having cut-off values in the range of 340-800 Da. The concentration of dimer saccharides and monomer saccharides in the fractions obtained by the purification method can be monitored by gel permeation chromatography. The content of (optionally reduced and/or oxidized and/or derivatized) oligosaccharide or polysaccharide in the fractions can be determined by optical rotation.

The amount of iron in the iron carbohydrate complex compound of the invention, determined for dry matter, is typically in the range of from 10 to 50 wt-%, such as from 15 to 45 wt-% and in particular from 24 to 32 wt-%. The concentration of iron in iron complex solutions for injection according to the invention is typically in the range of from 25 to 300 mg/ml, such as from 50 to 200 mg/ml. In preferred particular embodiments of iron complex solutions for injection according to the invention, the concentration of iron is about 100 mg/ml or about 200 mg/ml.

In particular embodiments, the carbohydrate is a hydrogenated polysaccharide or hydrogenated oligosaccharide or mixture thereof (hereinafter referred to as hydrogenated poly-/oligosaccharide) having a weight average $M_W$ of from 500 to 7,000 Da, such as from 500 to 3,000 Da, from 700 to 1,400 Da and in particular of about 1,000 Da. The number average molecular weight ($M_n$) of such hydrogenated poly-/oligosaccharide is preferably in the range of from 400 to 1,400 Da, and 90 wt-% of these molecules have molecular weights of less than 3,500 Da, in particular less than 2,700 Da, and the molecular weights of the remaining 10% of the molecules are below 4,500, in particular below 3,200 Da. For example, said hydrogenated poly-/oligosaccharide is a hydrogenated polyglucose, oligoglucose or mixture thereof, such as a hydrogenated dextran, hydrogenated dextrin or hydrogenated oligoisomaltose (oligoisomaltoside) or a mixture thereof, wherein hydrogenated oligoisomaltose, particularly hydrogenated oligoisomaltose wherein the majority (such as at least 60%, e.g. from 70 to 80%) of the molecules has 3-6 monosaccharide units, is preferred. Accordingly, in preferred embodiments of the invention, the iron complex compound is an iron hydrogenated oligoisomaltose, in particular an iron(III) hydrogenated oligoisomaltose, wherein the majority (such as at least 60%, e.g. from 70 to 80%) of the hydrogenated oligoisomaltoside molecules has 3-6 monosaccharide units, such as iron(III) isomaltoside 1000 (INN name: ferric derisomaltose). Iron isomaltosides are typically characterized by a strong colloidal complex of iron oxide-hydroxide and hydrogenated isomaltose (isomaltoside) chains resulting in a gradual release of iron.

In the particular embodiments described above, the content of dimer saccharide of the hydrogenated poly-/oligosaccharide is preferably 2.9 wt-% or less, in particular 2.5 wt-% or less, and especially 2.3 wt-% or less, based on the total weight of the hydrogenated poly-/oligosaccharide. Preferably, preparations of the hydrogenated poly-/oligosaccharide used for preparing iron carbohydrate complex compounds of the invention have a content of monomer saccharide of 0.5 wt-% or less. Iron hydrogenated dextran complex compounds prepared from such hydrogenated poly-/oligosaccharide preparations typically have an apparent molecular weight ($M_p$) in the range of from 120,000 to 180,000 Da, in particular from 130,000 to 160,000 Da. Before the hydrogenated poly-/oligosaccharide preparation is contacted with the iron preparation, the preparation can be purified by membrane processes so as to remove high molecular weight hydrogenated polysaccharides and/or low molecular weight hydrogenated oligosaccharides. In particular embodiments, the hydrogenated poly-/oligosaccharide preparation has been purified by one or more membrane processes having a cut-off value between 340 and 800 Da. In even more particular embodiments, the hydrogenated poly-/oligosaccharide preparation has been purified by one or more membrane processes using a membrane having a cut-off value that allows for holding back polysaccharides having a molecular weight above 2,700 Da, optionally followed by further hydrolysis, and followed by one or more membrane processes using a membrane having a cut-off value between 340 and 800 Da.

In a particularly preferred embodiment, the iron complex compound of the invention is a compound having the formula

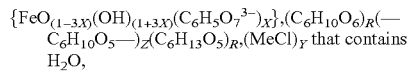

wherein
X is 0.0311±0.0062, in particular of 0.0311±0.0031;
R is 0.1400±0.0420, in particular 0.1400±0.0210;
Z is 0.4900±0.1470, in particular 0.4900±0.0735;
Y is 1.8000±1.0800, in particular 1.8000±0.4500; and
Me is a monovalent metal ion such as a sodium ion or potassium ion, and is preferably a sodium ion.

In a further particularly preferred embodiment, the iron complex compound of the invention is a compound having the formula

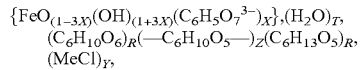

wherein
X is 0.0311±0.0062, in particular 0.0311±0.0031;
T is 0.2500±0.1250, in particular 0.2500±0.24750;
R is 0.1400±0.0420, in particular 0.1400±0.0210;
Z is 0.4900±0.1470, in particular 0.4900±0.0735;
Y is 1.8000±1.0800, in particular 1.8000±0.4500; and
Me is a monovalent metal ion such as a sodium ion or potassium ion, and is preferably a sodium ion.

In particular embodiments, the iron complex compound of the invention is an iron complex with an poly-/oligosaccharide (e.g. a polyglucose such as a dextran) that is both hydrogenated and oxidized as described herein. Such iron complex compound typically has an apparent molecular weight ($M_p$) in the range of from 50,000 to 150,000 Da, in particular from 70,000 to 130,000 Da, more particularly 80,000 to 120,000 Da.

In particular embodiments, the iron complex compound of the invention is an iron complex where the carbohydrate is a hydrogenated dextran with a weight average molecular weight ($M_w$) in the range of from 2,000 to 6,000 Da. In one of these particular embodiments, the iron complex has an iron content (determined for dry matter) of from 36 to 41 wt-% and, optionally is present in the form of an injectable solution having an iron content of about 200 mg/ml. In another of these particular embodiments, the iron complex has an iron content (determined for dry matter) of from 23 to 39 wt-% and is optionally present in the form of an injectable solution having about 100 mg/ml.

In another preferred embodiment, the iron complex is an iron dextran complex that complies with the British Pharmacopoeia and/or U.S. Pharmacopoeia monographs for Iron Dextran Injection.

Iron carbohydrate complex compounds of the invention can be prepared by
  (1) providing an aqueous solution that comprises a carbohydrate and an iron preparation as described herein comprising a water-soluble iron salt (e.g. ferric chloride),
  (2) adding a base to the aqueous solution so as to form iron hydroxide, and
  (3) then heating the aqueous solution so as to form the iron carbohydrate complex compound.

Preferably, the pH of the aqueous solution in step (1) is acidic, e.g. the solution is at a pH of 2 or lower, so as to prevent the precipitation of iron hydroxides. The addition of a base in step (2) is preferably performed in a slow or gradual manner so as to increase the pH to, for example, a pH of 5 or more, such as up to pH 11, 12, 13 or 14. Such gradual increase can be achieved by first adding a weak base (e.g., an alkali metal carbonate or alkaline earth metal carbonate such as sodium carbonate, potassium carbonate, sodium bicarbonate or potassium bicarbonate, or ammonia) to increase the pH, e.g., up to pH 2-4, e.g., up to 2-3, and then further increasing the pH by adding a strong base (e.g., an alkali metal hydroxide or alkaline earth metal hydroxide such as sodium hydroxide, potassium hydroxide, calcium hydroxide or magnesium hydroxide).

Alternatively, iron carbohydrate complex compounds of the invention can be prepared by
  (1) providing an aqueous solution that comprises a carbohydrate and an iron preparation as described herein comprising an iron hydroxide, iron oxide-hydroxide or a mixture thereof, and
  (2) then heating the aqueous solution so as to form the iron carbohydrate complex compound.

The heating of the aqueous solution in the last step of the two above-described processes for preparing iron carbohydrate complex compounds of the invention facilitates the formation of the iron carbohydrate complex compound. For example, the aqueous solution may be heated to a temperature in the range of from 15° C. to boiling. Preferably, the temperature is gradually increased, for example in a first step the aqueous solution is heated to a temperature of from 15 to 70° C. and then is gradually heated further until boiling. To finalize the reaction the pH can be reduced to, e.g., pH 5-6 by adding an acid such as, for example, HCl or aqueous hydrochloric acid. In one embodiment, said reduction of pH is performed when the solution has been heated to about 50° C. and before it is further heated.

After heating, the product can be further processed by filtration and its pH can be adjusted to a neutral or slightly acidic pH (e.g., pH 5 to 7) by adding a base or acid such as those mentioned above. Further optional steps include purification, in particular the removal of salts, which may be achieved by ultrafiltration or dialysis, and sterilization which may be achieved by filtration and/or heat treatment (e.g., at temperatures of 121° C. or higher). The purified solution can be used directly for preparing pharmaceutical compositions. Alternatively, solid iron carbohydrate complex can be obtained by precipitation, e.g. by adding an alcohol such as ethanol, or by drying, e.g. spray-drying.

The iron carbohydrate complex compound can be stabilized by mixing it with an organic hydroxyl acid or salt thereof such as citric acid, a citrate or a gluconate.

According to another group of embodiments, the iron complex compound is a polymeric ligand-substituted oxo-hydroxy iron complex compound. Polymeric ligand-substituted oxo-hydroxy iron complex compounds comprise or basically consist of iron ions (e.g., $Fe^{3+}$), ligands and oxo and/or hydroxyl groups. The iron ions, oxo and/or hydroxyl groups form poly oxo-hydroxy iron particles. The ligands are incorporated therein through substitution of part of the initially present oxo or hydroxyl groups. This substitution is generally non-stoichiometrical, occurs through formal bonding and leads to distinct alterations in the chemistry, crystallinity and material properties of the oxo-hydroxy iron. Polymeric ligand-substituted oxo-hydroxy iron complex compounds are described, for example, in WO 2008/096130 A1.

Suitable ligands for ligand-substituted oxo-hydroxy iron complex compounds of the invention include, for example, carboxylic acids, such as adipic acid, glutaric acid, tartaric acid, malic acid, succinic acid, aspartic acid, pimelic acid, citric acid, gluconic acid, lactic acid and benzoic acid; food additives such as maltol, ethyl maltol and vanillin; anions with ligand properties such as bicarbonate, sulphate and phosphate; mineral ligands such as silicate, borate, molybdate and selenate; amino acids, in particular proteinogenic amino acids, such as tryptophan, glutamine, proline, valine and histidine; and nutrient-based ligands such as folate, ascorbate, pyridoxine and niacin; as well as a mixtures of two or more thereof.

The average molar ratio of ligand to iron is typically in the range of from 10:1 to 1:10, such as in the range of from 5:1 to 1:5, from 4.1 to 1:4, from 3.1 to 1:3, from 2:1 to 1:2 or at about 1:1.

Polymeric ligand-substituted oxo-hydroxy iron complex compounds of the invention can be prepared by contacting an iron preparation as described herein that is low in arsenic and lead, and optionally is also low in chromium, mercury, cadmium and/or aluminum with a ligand in an aqueous solution at a first pH(A) and then changing the pH(A) to a second pH(B) to cause a solid precipitation of the polymeric ligand-substituted oxo-hydroxy iron complex compound. The solid precipitate can have a particulate, colloidal or sub-colloidal (nanoparticulate) structure.

The pH(A) is different from the pH(B). Preferably, the pH(A) is more acidic than the pH(B). For example, pH(A) is equal or below pH 2 and pH(B) is above pH 2. Starting from the pH at which oxo-hydroxy polymerization commences, the pH is preferably further increased to complete the reaction and promote precipitation of the polymeric ligand-substituted oxo-hydroxy iron complex compound formed. During said pH change further ligands and/or excipients can be added. Said pH change is preferably done in a gradual or stepwise manner, for example over a period of about 24 hours or over a period of about 1 hour, and in particular over a period of 20 minutes. The pH change can be effected by the addition of acids or bases. For example, the pH can be increased by adding sodium hydroxide, potassium hydroxide or sodium bicarbonate.

The polymeric ligand-substituted oxo-hydroxy iron complex compounds are typically produced in aqueous solutions, wherein the concentrations of iron ions and ligand are 1 μM or higher and in particular 1 mM or higher. The ratio of iron ions and ligand is chosen such that the relative amount of iron ions is not too high such that the rate of oxo-hydroxy polymerization occurs too rapidly and efficient ligand incorporation is prevented, and the relative amount of ligand is not too high to prevent iron oxo-hydroxy polymerization. For example, the iron concentration is in the range of from 1 mM to 300 mM, such as from 20 mM to 200 mM and in particular at about 40 mM.

The ligands used for the formation of the polymeric ligand-substituted oxo-hydroxy iron complex compounds may have some buffering capacity which helps to stabilizing the pH range during complex formation. Buffering can also be achieved by adding an inorganic or organic buffering agent, which will not be involved in formal bonding with the iron ions, to the aqueous solution containing the iron preparation and the ligand. Typically, the concentration of such buffer, if present, is less than 500 mM or less than 200 mM, and in particular less than 100 mM.

The formation of the polymeric ligand-substituted oxo-hydroxy iron complex compounds typically takes place at a temperature within the range of from 20° C. to 120° C., e.g., 20° C. to 100° C., in particular from 20 to 30° C.

Optionally, the ionic strength in the aqueous solution comprising the iron preparation and the ligand can be increased by adding further electrolyte such as, e.g., potassium chloride or sodium chloride in an amount of, e.g., up to 10 wt-%, such as up to 2 wt-%, and in particular up to 1 wt-%.

The solid precipitate of polymeric ligand-substituted oxo-hydroxy iron complex compound can be separated and optionally be dried and processed further by, e.g., grinding before further use or formulation.

The present invention also relates to iron complex compounds obtainable by a process of the invention as describe herein.

The present invention also relates to iron complex compounds, wherein the amount of arsenic does not exceed 4.5 μg per g iron, for example does not exceed 3.0 μg per g iron, 2.5 μg per g iron or 2.0 μg per g iron, and in particular does not exceed 1.5 μg per g iron, for example does not exceed 1.0 μg per g iron, 0.8 μg per g iron, 0.5 μg per g iron or 0.3 μg per g iron; and the amount of lead does not exceed 1.5 μg per g iron, 1.3 μg per g iron, 1.0 μg per g iron or 0.7 μg per g iron, and in particular does not exceed 0.5 μg per g iron, for example does not exceed 0.4 μg per g iron or 0.2 μg per g iron; and optionally, the amount of cadmium does not exceed 0.6 μg per g iron, for example does not exceed 0.5 μg per g iron, and in particular does not exceed 0.4 µg per g iron, for example does not exceed 0.3 µg per g iron or 0.2 µg per g iron; and optionally, the amount of mercury does not exceed 0.9 µg per g iron, for example does not exceed 0.7 µg per g iron or 0.5 µg per g iron, and in particular does not exceed 0.3 µg per g iron, for example does not exceed 0.2 µg per g iron or 0.10 µg per g iron; and optionally, the amount of chromium does not exceed 330 µg per g iron, for example does not exceed 250 µg per g iron or 170 µg per g iron, and in particular does not exceed 100 µg per g iron, for example does not exceed 75 µg per g iron, 50 µg per g iron or 20 µg per g iron; and optionally, the amount of aluminum does not exceed 200 µg per g iron, for example does not exceed 150 µg per g iron, 100 µg per g iron or 50 µg per g iron, and in particular does not exceed 25 µg per g iron, for example does not exceed 20 µg per g iron or 15 µg per g iron.

In a $1^{st}$ embodiment, the iron complex compound of the invention is characterized in that the amount of arsenic does not exceed 4.5 µg per g iron; and the amount of lead does not exceed 1.5 µg per g iron; and optionally, the amount of aluminum does not exceed 200 µg per g iron, in particular does not exceed 150 µg per g iron and preferably does not exceed 100 µg per g iron.

In a $2^{nd}$ embodiment, the iron complex compound of the invention is characterized in that the amount of arsenic does not exceed 4.5 µg per g iron; and the amount of lead does not exceed 1.5 µg per g iron; and the amount of cadmium does not exceed 0.6 µg per g iron; and the amount of mercury does not exceed 0.9 µg per g iron; and optionally, the amount of aluminum does not exceed 200 µg per g iron, in particular does not exceed 150 µg per g iron and preferably does not exceed 100 µg per g iron.

In a $3^{rd}$ embodiment, the iron complex compound of the invention is characterized in that the amount of arsenic does not exceed 4.5 µg per g iron; and the amount of lead does not exceed 1.5 µg per g iron; and the amount of cadmium does not exceed 0.6 µg per g iron; and the amount of mercury does not exceed 0.9 µg per g iron; and the amount of chromium does not exceed 330 µg per g iron; and optionally, the amount of aluminum does not exceed 200 µg per g iron, in particular does not exceed 150 µg per g iron and preferably does not exceed 100 µg per g iron.

In a $4^{th}$ embodiment, the iron complex compound of the invention is characterized in that the amount of arsenic does not exceed 1.5 µg per g iron; and the amount of lead does not exceed 0.5 µg per g iron.

In a $5^{th}$ embodiment, the iron complex compound of the invention is characterized in that the amount of arsenic does not exceed 1.5 µg per g iron; and the amount of lead does not exceed 0.5 µg per g iron; and the amount of cadmium does not exceed 0.4 µg per g iron; and the amount of mercury does not exceed 0.3 µg per g iron.

In a $6^{th}$ embodiment, the iron complex compound of the invention is characterized in that the amount of arsenic does not exceed 1.5 µg per g iron; and the amount of lead does not exceed 0.5 µg per g iron; and the amount of cadmium does not exceed 0.4 µg per g iron; and the amount of mercury does not exceed 0.3 µg per g iron; and the amount of chromium does not exceed 100 µg per g iron.

In a $7^{th}$ embodiment, the iron complex compound of the invention is characterized in that the amount of arsenic does not exceed 1.5 µg per g iron; and the amount of lead does not exceed 0.5 µg per g iron; and the amount of cadmium does not exceed 0.4 µg per g iron; and the amount of mercury does not exceed 0.3 µg per g iron; and the amount of chromium does not exceed 100 µg per g iron; and the amount of aluminum does not exceed 25 µg per g iron.

In a 8th embodiment, the iron complex compound of the invention is characterized in that the amount of arsenic does not exceed 1.5 µg per g iron; and the amount of lead does not exceed 0.5 µg per g iron; and the amount of cadmium does not exceed 0.4 µg per g iron; and the amount of mercury does not exceed 0.3 µg per g iron; and the amount of chromium does not exceed 100 µg per g iron; and the amount of aluminum does not exceed 20 µg per g iron.

In a $9^{th}$ embodiment, the iron complex compound of the invention is characterized in that the amount of arsenic does not exceed 1.5 µg per g iron; and the amount of lead does not exceed 0.5 µg per g iron; and the amount of cadmium does not exceed 0.4 µg per g iron; and the amount of mercury does not exceed 0.3 µg per g iron; and the amount of chromium does not exceed 100 µg per g iron; and the amount of aluminum does not exceed 15 µg per g iron.

An iron complex compound according to any one of said $1^{st}$ to $9^{th}$ embodiments, or a composition thereof, can be used for treatment or prophylaxis of iron-deficiency in a subject. The subject may be a human subject or a non-human animal, in particular a non-human mammal, e.g. a pig, horse, dog, cat, camel, sheep, goat or cow. In case of iron complex compounds according to any one of said $1^{st}$ to $3^{rd}$ embodiments, and compositions thereof, the subject is preferably a human subject. In case of iron complex compounds according to any one of said $4^{th}$ to $9^{th}$ embodiments, and compositions thereof, the subject is preferably an infant of a non-human animal, in particular an animal for food production (e.g., milk and/or meat production), such as a piglet.

An iron complex compound according to any one of said $1^{st}$ to $9^{th}$ embodiments can be formulated, and used, for various ways of administration, for example for intramuscular administration or for intravenous administration. Iron complex compounds according to any one of said $1^{st}$ to $3^{rd}$ embodiments are preferably formulated, and used, for intravenous administration. Iron complex compounds according to any one of said 4th to 9$^{th}$ embodiments are preferably formulated, and used, for intramuscular administration.

The present invention also relates to iron complex compounds, wherein
the amount of aluminum does not exceed 200 µg per g iron, for example does not exceed 150 µg per g iron, 100 µg per g iron or 50 µg per g iron, and in particular does not exceed 25 µg per g iron, for example does not exceed 20 µg per g iron or 15 µg per g iron; and
optionally, the amount of arsenic does not exceed 4.5 µg per g iron, for example does not exceed 3.0 µg per g iron, 2.5 µg per g iron or 2.0 µg per g iron, and in particular does not exceed 1.5 µg per g iron, for example does not exceed 1.0 µg per g iron, 0.8 µg per g iron, 0.5 µg per g iron or 0.3 µg per g iron; and
optionally, the amount of lead does not exceed 1.5 µg per g iron, 1.3 µg per g iron, 1.0 µg per g iron or 0.7 µg per g iron, and in particular does not exceed 0.5 µg per g iron, for example does not exceed 0.4 µg per g iron or 0.2 µg per g iron; and
optionally, the amount of cadmium does not exceed 0.6 µg per g iron, for example does not exceed 0.5 µg per g iron, and in particular does not exceed 0.4 µg per g iron, for example does not exceed 0.3 µg per g iron or 0.2 µg per g iron; and
optionally, the amount of mercury does not exceed 0.9 µg per g iron, for example does not exceed 0.7 µg per g iron or 0.5 µg per g iron, and in particular does not exceed 0.3 µg per g iron, for example does not exceed 0.2 µg per g iron or 0.10 µg per g iron; and
optionally, the amount of chromium does not exceed 330 µg per g iron, for example does not exceed 250 µg per g iron or 170 µg per g iron, and in particular does not exceed 100 µg per g iron, for example does not exceed 75 µg per g iron, 50 µg per g iron or 20 µg per g iron.

In one embodiment, the iron complex compound of the invention is characterized in that
the amount of aluminum does not exceed 200 µg per g iron.

In a further embodiment, the iron complex compound of the invention is characterized in that
the amount of aluminum does not exceed 150 µg per g iron.

In a further embodiment, the iron complex compound of the invention is characterized in that
the amount of aluminum does not exceed 100 µg per g iron.

An iron complex compound according to any one of afore-mentioned three embodiments, or a composition thereof, can be used for treatment or prophylaxis of iron-deficiency in a subject. The subject may be a human subject or a non-human animal, in particular a non-human mammal, e.g. a pig, horse, dog, cat, camel, sheep, goat or cow. Preferably, the subject is a human subject.

An iron complex compound according to any one of afore-mentioned three embodiments can be formulated, and used, for various ways of administration, for example for intramuscular administration or for intravenous administration.

The invention further provides compositions comprising an iron complex compound of the invention as described herein and a pharmaceutically acceptable carrier. The form of the composition is chosen depending on the intended mode of administration. The composition may therefore be adapted for oral, parenteral or other forms of administration.

Examples of compositions for oral use include granules, tablets, capsules (e.g., hard gelatin capsules or soft gelatin capsules) and liquid preparations such as solutions and suspensions. Tablets and capsules can be prepared by conventional means using pharmaceutically acceptable carriers such as, e.g., pregelatinised maize starch, polyvinylpyrrolidone, hydroxypropyl methylcellulose, lactose, microcrystalline cellulose or calcium hydrogen phosphate, and further excipients such as lubricants (e.g., magnesium stearate, talc, or silica); disintegrants (e.g., potato starch or sodium starch glycolate); or wetting agents (e.g., sodium lauryl sulfate). Tablets may be coated using methods well-known in the art. Liquid preparations for oral administration may take the form of, e.g., solutions, syrups or suspensions, or may be presented as a dry product for constitution with water or other suitable liquid before use. Such liquid preparations can be prepared by conventional means and include pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); preservatives (e.g., methyl or propyl-p-hydroxybenzoates or sorbic acid); buffer salts, flavoring, coloring agents and/or sweetening agents. Compositions for oral administration can be formulated for slow release, controlled release or sustained release of the iron complex compound.

Compositions for parenteral administration can have the form of injectable or infusible solutions, suspensions or emulsions in liquid carriers such as, for example, sterile water, saline or other buffered aqueous solutions. Such compositions may comprise further additives such as stabilizing agents (e.g., citric acid, citrate or gluconate), antibacterial agents (e.g., benzyl alcohol or phenol), antioxidants (e.g., ascorbic acid or sodium bisulfite) and/or agents for adjusting tonicity (e.g., sodium chloride or dextrose). Alternatively, the iron complex compound may be presented in the form of a powder for constitution with sterile water or saline or another suitable liquid before use. Compositions for parenteral administration may also be formulated as implantable or injectable depot compositions, for example with suitable polymeric or hydrophobic carriers.

In particular embodiments, the compositions of the invention are formulated for parenteral administration (e.g., intramuscular injection, subcutaneous injection, intravenous injection or intravenous infusion, optionally as bolus injection or infusion) such as, for example, as injectable or infusible solutions in an aqueous carrier such as saline.

The compositions of the invention may comprise additional nutritional or pharmaceutical agents such as, e.g., vitamins, in particular water-soluble vitamins, micronutrients such as, e.g., cobalt, copper, zinc or selenium, erythropoietin, bacteriostatic agents or antibiotics. Water-insoluble vitamins may be incorporated into aqueous compositions of the invention by way of emulsification.

The invention provides iron complex compounds of the invention as described herein for therapeutic use. Accordingly, methods for administering an iron complex compound of the invention to a subject are described herein. The iron complex compound can be administered, for example, orally or parenterally (such as by intramuscular injection, subcutaneous injection, intravenous injection or intravenous infusion, optionally as bolus injection or infusion). The iron complex compound can be administered in the form of a composition thereof as described herein.

In particular, iron complex compounds of the invention can be used for the treatment or prophylaxis of iron-deficiency in a subject. The subject can be selected from, for example, pig, horse, dog, cat, camel, sheep, goat, cow and human.

The iron complex compounds of the invention are also useful for the treatment or prophylaxis of iron-deficiency in infants such as, e.g., children, piglets, foals, camel foals, lambs, goat kids or calfs.

The term infant as used herein includes non-adult offspring starting from neonates.

Iron deficiency that can be treated or prevented by administering an iron complex compound of the invention can be, for example, iron deficiency associated with chronic blood loss, acute blood loss, pregnancy, childbirth, lactation, childhood development, heavy uterine bleeding, menstruation, gastrointestinal bleeding, chronic internal bleeding, inflammatory bowel disease, congestive heart failure, restless leg syndrome, parasitic infections, lost or impaired kidney function such as due to chronic kidney disease or kidney failure, dialysis, surgery, chronic ingestion of agents such as alcohol, salicylates, steroids, non-steroidal anti-inflammatory agents, erythropoiesis stimulating agents (ESAs) or drugs inhibiting iron absorption.

The iron complex compounds of the invention are in particular useful for the treatment or prophylaxis of iron-deficiency in a pregnant mammal, a mammal expected to become pregnant (such as a mammal prior to insemination) or a nursing mammal. It is recognized that the blood hemoglobin level of mammals such as sows will decrease with increasing parity. According to particular embodiments, an iron complex compound of the invention is used for the treatment or prophylaxis of iron-deficiency in a mammal of second or higher parity, such as third parity, such as forth parity, such as fifth parity, such as sixth parity, such as seventh parity, such as eighth parity or higher, that is pregnant or expected to become pregnant. The iron complex compounds of the invention can be administered to the mammal at one or more points before and/or during pregnancy, such as two, three, four, five, six or more doses during pregnancy, e.g. over a period of 15 weeks to 2 weeks prior to delivery. The iron complex compounds can be administered together with other nutritional or pharmaceutical agents such as, e.g., vitamins, micronutrients such as, e.g., cobalt, copper, zinc or selenium, erythropoietin, bacteriostatic agents or antibiotics. The treatment or prophylaxis of iron deficiency in pregnant mammals or mammals expected to become pregnant using iron complex compounds of the invention can decrease the rate of stillborn infants. The use of an iron complex compound of the invention for the treatment or prophylaxis of iron deficiency in a pregnant mammal or a mammal expected to become pregnant or a nursing mammal can increase the survival, health and/or growth of the offspring until weaning and can treat or prevent an iron deficiency in a fetus or infant to be born or nursed by said mammal. This includes the treatment or prevention of iron deficiency in the brain of a fetus or infant. Iron deficiency in the brain of a fetus or infant may cause abnormal development of the fetal or infant brain and is associated with diseases and disorders such as restless leg syndrome (RLS), attention deficit hyperactivity disorder (ADHD), attention deficit disorder (ADD), absence seizure, bipolar disorder, schizophrenia, obsessive-compulsive disorder (OCD), autism and borderline personality disorder (BPD). See WO 2016/206699 A1. An iron complex compound of the invention can therefore be used for treating or preventing iron deficiency in a fetus or infant, in particular iron deficiency in the brain of a fetus or infant, by administering the iron complex compound to the mother of the fetus or infant or to the mammal nursing the infant, wherein the iron complex compound can be administered to the mother during the phase prior to pregnancy and/or during pregnancy and/or during nursing.

The iron complex compounds of the invention are also useful for the treatment or prophylaxis of iron-deficiency in a human suffering from lost or impaired kidney function, for example a human in need of dialysis. Humans with lost or impaired kidney function are often low in erythropoietin and receive drugs such as ESAs to allow for sufficient erythrogenesis. Erythrogenesis induced by ESAs can use up the patient's iron reserves faster than normal, thus increasing the risk of iron deficiency. Moreover, the diet of human patients on dialysis may limit the intake of certain iron-rich foods such as red meat and beans, and thus the ability of the patients to take up sufficient iron with their diet. Further, frequent blood sampling for laboratory testing, surgical procedures for vascular access as well as blood loss into the hemodialyzer and tubing are further factors which contribute to iron loss of the patients. Humans suffering from lost or impaired kidney function, and especially humans in need of dialysis on dialysis, are therefore at particular risk of iron-deficiency.

The amount of aluminum in the iron complex compound of the invention for administration to a human subject, in particular a patient suffering from lost or impaired kidney function, such as a patient in need of dialysis, preferably does not exceed 200 µg per g of iron, for example does not exceed 150 µg per g iron, 100 µg per g iron or 50 µg per g iron, and in particular does not exceed 25 µg per g iron, 20 µg per g iron or 15 µg per g iron.

The amount of aluminum in the iron complex compound of the invention for administration to an infant of a non-human animal subject, in particular an infant of a non-human mammal, e.g. a piglet, preferably does not exceed 25 µg per g iron, for example does not exceed 20 µg per g iron or 15 µg per g iron.

The iron complex compound of the invention is suitable for being administered to a subject at a dose containing 200 mg or more iron within 2 minutes or less.

A single dose of iron complex compound of the invention may contain 200 mg iron or more, 500 mg iron or more, such as 750 mg iron or more, for example 500 to 1000 mg iron.

The iron complex compound of the invention can be administered to a subject, such as a human, at an amount of up to 5 mg iron per kg bodyweight of the subject in one sitting, up to 10 mg iron per kg bodyweight of the subject in one sitting, up to 15 mg iron per kg bodyweight of the subject in one sitting or even up to 20 mg iron per kg bodyweight of the subject in one sitting, such as for example 15 to 20 mg iron per kg bodyweight of the subject in one sitting.

The amount of iron complex compound of the invention that can be administered to a subject such as a piglet can be even higher such as up to 50 mg iron per kg bodyweight in one sitting, up to 100 mg iron per kg bodyweight in one sitting or up to 200 mg iron per kg bodyweight in one sitting, for example about 200 mg iron per kg bodyweight of the subject in one sitting.

The use of an iron complex compound of the invention for the treatment or prophylaxis of iron deficiency may comprise administration of one dose of iron complex compound containing an amount of 200 mg or more iron every four weeks or more frequently, for example every three weeks or more frequently, every two weeks or more frequently, or every week or more frequently.

In addition to uses as therapeutic iron supplements, the iron complex compounds of the invention can also be used, for example, as dietary mineral supplement or fortificant, anti-hematinic drug or iron based phosphate binding agent. For said additional uses the iron complex compound is usually administered orally.

The present invention further relates to the following embodiments E1 to E68.

E1. A process for preparing an iron complex compound comprising the steps of
  (i) providing an iron preparation comprising iron in a form selected from a water-soluble iron salt, an iron hydroxide or an iron oxide-hydroxide, wherein
    the amount of arsenic in the iron preparation does not exceed 4.5 µg per g of iron, and
    the amount of lead in the iron preparation does not exceed 1.5 µg per g of iron; and
  (ii) contacting the iron preparation with a ligand in the presence of water so as to form the iron complex compound.

E2. The process of E2, wherein
  the amount of cadmium in the iron preparation does not exceed 0.6 µg per g of iron, and
  the amount of mercury in the iron preparation does not exceed 0.9 µg per g of iron.

E3. The process of E1 or E2, wherein
  the amount of chromium in the iron preparation does not exceed 330 µg per g of iron.

E4. The process of any one of E1-E3, wherein the amount of aluminum in the iron preparation does not exceed 200 µg per g of iron.

E5. The process of any one of E1-E4, wherein the iron preparation is obtained
  (a) from iron pentacarbonyl; or
  (b) by recrystallization of an iron salt from an aqueous solution thereof; or
  (c) by extracting an aqueous iron salt solution with an organic solvent; or
  (d) from iron precipitated at an anode during electrolysis of an aqueous iron salt solution; or
  (e) by contacting an aqueous iron salt solution with a base so as to form a precipitate of iron hydroxide and separating the precipitate from the liquid by filtration or centrifugation; or
  (f) by distillation of ferric chloride from a mixture comprising ferric chloride and non-volatile impurities.

E6. The process of E5, wherein the recrystallization of an iron salt from an aqueous solution thereof is the recrystallization of ferric nitrate from an aqueous solution containing nitric acid.

E7. The process of E5, wherein the iron salt is ferric chloride, and the organic solvent is an alcohol having from 4 to 20 carbon atoms, in particular from 6 to 10 carbon atoms, or an organic solution of an amine salt.

E8. The process of E5, wherein the electrolysis of an aqueous iron salt solution is the electrolysis of an aqueous solution comprising iron chloride or iron sulfate.

E9. The process of E5, wherein the base with which the aqueous iron salt solution is contacted is selected from sodium hydroxide, sodium bicarbonate and sodium carbonate.

E10. The process of any one of E1-E9, wherein the iron preparation comprises a water-soluble iron salt that is obtained by converting an iron hydroxide, iron oxide-hydroxide or a mixture thereof to a water-soluble iron salt.

E11. The process of any one of E1-E10, wherein the iron complex compound is an iron carbohydrate complex compound.

E12. The process of E11, wherein the content of reducing aldehyde groups in the carbohydrate that serves as ligand in the iron complex compound has been reduced by oxidation,
  hydrogenation, or
  a combination of both.

E13. The process of E11 or E12, wherein the iron preparation of step (i) comprises a water soluble iron salt and the step (ii) of the process comprises
  (1) providing an aqueous solution comprising the iron preparation and a carbohydrate,
  (2) adding a base to the aqueous solution so as to form iron hydroxide, and
  (3) then heating the aqueous solution so as to form the iron carbohydrate complex compound.

E14. The process of E11 or E12, wherein the iron preparation of step (i) comprises an iron hydroxide or an iron oxide-hydroxide and the step (ii) of the process comprises:
  (1) providing an aqueous solution comprising the iron preparation and a carbohydrate, and
  (2) then heating the aqueous solution so as to form the iron carbohydrate complex compound.

E15. The process of any one of E11-E14, wherein the iron carbohydrate complex compound is selected from iron carboxymaltose, iron polyglucose sorbitol carboxymethyl ether complex, iron mannitol complex, iron dextran, iron hydrogenated dextran, iron oxidized dextran, iron carboxyalkylated reduced oligo- and polysaccharides, iron sucrose, iron gluconate, iron dextrin, iron hydrogenated dextrin, iron oxidized dextrin, iron polymaltose, iron hydrogenated polymaltose, iron polyisomaltose, iron hydrogenated polyisomaltose, iron hydrogenated oligosaccharides such as iron hydrogenated oligoisomaltose, iron hydroxyethyl starch, iron sorbitol, iron dextran glucoheptonic acid and a mixture of two or more thereof.

E16. The process of any one of E11-E15, wherein the iron carbohydrate complex compound is selected from iron carboxymaltose, iron polyglucose sorbitol carboxymethyl ether complex, iron mannitol complex, iron dextran, iron hydrogenated dextran, iron sucrose, iron gluconate, iron dextrin, iron hydrogenated oligoisomaltose and a mixture of two or more thereof.

E17. The process of any one of E11-E16, wherein the carbohydrate component of the iron carbohydrate complex compound has a weight average molecular weight ($M_W$) of from 500 to 80,000 Da.

E18. The process of any one of E11-E17, wherein the apparent molecular weight of the iron carbohydrate complex compound is in the range of from 800 to 800,000 Da.

E19. The process of any one of E1-E10, wherein the iron complex compound is a polymeric ligand-substituted oxo-hydroxy iron complex compound.

E20. The process of E19, wherein step (ii) of the process comprises
  (1) contacting the iron preparation with the ligand in an aqueous solution at a first pH(A); and
  (2) changing the pH(A) to a second pH(B) to cause a solid precipitation of the polymeric ligand-substituted oxo-hydroxy iron complex compound.

E21. The process of E19 or E20, wherein the ligand is selected from a carboxylic acid, such as adipic acid, glutaric acid, tartaric acid, malic acid, succinic acid, aspartic acid, pimelic acid, citric acid, gluconic acid, lactic acid and benzoic acid; flavoring agents such as maltol, ethyl maltol and vanillin; an anion with ligand properties such as bicarbonate, sulphate and phosphate; a mineral ligand such as silicate, borate, molybdate and selenate; an amino acid such as tryptophan, glutamine, proline, valine and histidine; and a nutrient-based ligand such as folate, ascorbate, pyridoxine and niacin; and a mixture of two or more thereof.

E22. The process of any one of E19-E21, wherein the average molar ratio of ligand to iron is in the range of from 10:1 to 1:10.

E23. The process of any one of E1-E22, further comprising the step of mixing the iron complex compound with a compound selected from citric acid, a citrate and a gluconate.

E24. An iron complex compound obtainable by the process of any one of E1-E23.

E25. An iron complex compound, wherein
the amount of arsenic in the iron complex compound does not exceed 4.5 μg per g iron, and
the amount of lead in the iron complex compound does not exceed 1.5 μg per g iron.

E26. The iron complex compound of E25, wherein
the amount of arsenic in the iron complex compound does not exceed 1.5 μg per g of iron, and
the amount of lead in the iron complex compound does not exceed 0.5 μg per g of iron.

E27. The iron complex compound of E25 or E26, wherein
the amount of cadmium in the iron complex compound does not exceed 0.6 μg per g of iron, and
the amount of mercury in the iron complex compound does not exceed 0.9 μg per g of iron.

E28. The iron complex compound of E27, wherein
the amount of cadmium in the iron complex compound does not exceed 0.4 μg per g of iron, and
the amount of mercury in the iron complex compound does not exceed 0.3 μg per g of iron.

E29. The iron complex compound of any one of E25-E28, wherein
the amount of chromium in the iron complex compound does not exceed 330 μg per g of iron.

E30. The iron complex compound of E29, wherein
the amount of chromium in the iron complex compound does not exceed 100 μg per g of iron.

E31. The iron complex compound of any one of E25-E30, wherein
the amount of aluminum in the iron complex compound does not exceed 200 μg per g of iron.

E32. The iron complex compound of E31, wherein the amount of aluminum in the iron complex compound does not exceed 100 μg per g of iron.

E33. The iron complex compound of E32, wherein the amount of aluminum in the iron complex compound does not exceed 25 μg per g of iron.

E34. An iron complex compound, wherein the amount of aluminum in the iron complex compound does not exceed 200 μg per g iron.

E35. The iron complex compound of E34, wherein the amount of aluminum in the iron complex compound does not exceed 100 μg per g iron.

E36. The iron complex compound of E34, wherein the amount of aluminum in the iron complex compound does not exceed 25 μg per g iron.

E37. The iron complex compound of any one of E34-E36, wherein
the amount of arsenic in the iron complex compound does not exceed 4.5 μg per g iron, and
the amount of lead in the iron complex compound does not exceed 1.5 μg per g iron.

E38. The iron complex compound of E37, wherein
the amount of arsenic in the iron complex compound does not exceed 1.5 μg per g of iron, and
the amount of lead in the iron complex compound does not exceed 0.5 μg per g of iron.

E39. The iron complex compound of any one of E34-E38, wherein
the amount of cadmium in the iron complex compound does not exceed 0.6 μg per g of iron, and
the amount of mercury in the iron complex compound does not exceed 0.9 μg per g of iron.

E40. The iron complex compound of E39, wherein
the amount of cadmium in the iron complex compound does not exceed 0.4 μg per g of iron, and
the amount of mercury in the iron complex compound does not exceed 0.3 μg per g of iron.

E41. The iron complex compound of any one of E34-E40, wherein
the amount of chromium in the iron complex compound does not exceed 330 μg per g of iron.

E42. The iron complex compound of E41, wherein
the amount of chromium in the iron complex compound does not exceed 100 μg per g of iron.

E43. The iron complex compound of any one of E24-E42, wherein the iron complex compound is an iron carbohydrate complex compound.

E44. The iron complex compound of E43, wherein the content of reducing aldehyde groups in the carbohydrate that serves as ligand in the iron complex compound has been reduced by
oxidation,
hydrogenation, or
a combination of both.

E45. The iron complex compound of E43, wherein the iron carbohydrate complex compound is selected from iron carboxymaltose, iron polyglucose sorbitol carboxymethyl ether complex, iron mannitol complex, iron dextran, iron hydrogenated dextran, iron oxidized dextran, iron carboxyalkylated reduced oligo- and polysaccharides, iron sucrose, iron gluconate, iron dextrin, iron hydrogenated dextrin, iron oxidized dextrin, iron polymaltose, iron hydrogenated polymaltose, iron polyisomaltose, iron hydrogenated polyisomaltose, iron hydrogenated oligosaccharides such as iron hydrogenated oligoisomaltose, iron hydroxyethyl starch, iron sorbitol, iron dextran glucoheptonic acid and a mixture of two or more thereof.

E46. The iron complex compound of E43, wherein the iron carbohydrate complex compound is selected from iron carboxymaltose, iron polyglucose sorbitol carboxymethyl ether complex, iron mannitol complex, iron dextran, iron hydrogenated dextran, iron sucrose, iron gluconate, iron dextrin, iron hydrogenated oligoisomaltose and a mixture of two or more thereof.

E47. The iron complex compound of any one of E43-E46, wherein the carbohydrate component of the iron carbohydrate complex compound has a weight average molecular weight ($M_W$) of from 500 to 80,000 Da.

E48. The iron complex compound of any one of E43-E47, wherein the apparent molecular weight of the iron carbohydrate complex compound is in the range of from 800 to 800,000 Da.

E49. The iron complex compound of any one of E24-E42, wherein the iron complex compound is a polymeric ligand-substituted oxo-hydroxy iron complex compound.

E50. The iron complex compound of E49, wherein the polymeric ligand-substituted oxo-hydroxy iron complex compound is obtained by
(1) contacting an iron preparation with the ligand in an aqueous solution at a first pH(A); and
(2) changing the pH(A) to a second pH(B) to cause a solid precipitation of the polymeric ligand-substituted oxo-hydroxy iron complex compound.

E51. The iron complex compound of E49 or E50, wherein the ligand is selected from a carboxylic acid, such as adipic acid, glutaric acid, tartaric acid, malic acid, succinic acid, aspartic acid, pimelic acid, citric acid, gluconic acid, lactic acid and benzoic acid; a food additive such as maltol, ethyl maltol and vanillin; an anion with ligand properties such as bicarbonate, sulphate and phosphate; a mineral ligand such as silicate, borate, molybdate and selenate; an amino acid such as tryptophan, glutamine, proline, valine and histidine; and a nutrient-based ligand such as folate, ascorbate, pyridoxine and niacin; and a mixture of two or more thereof.

E52. The iron complex compound of any one of E24-E51, wherein the iron complex compound is stabilized with a compound selected from citric acid, a citrate and a gluconate.

E53. The iron complex compound of any one of E24-E52 having the formula $$\{FeO_{(1-3X)}(OH)_{(1+3X)}(C_6H_5O_7^{3-})_X\}_{x}(C_6H_{10}O_6)_R(-C_6H_{10}O_5^-)_Z(C_6H_{13}O_5)_R(MeCl)_Y \text{ that contains } H_2O,$$

wherein
X is 0.0311±0.0062, R is 0.1400±0.0420, Z is 0.4900±0.1470, Y is 1.8000±1.0800, and Me is a monovalent metal ion.

E54. The iron complex compound of E53, wherein X is 0.0311±0.0031, R is 0.1400±0.0210, Z is 0.4900±0.0735, Y is 1.8000±0.4500.

E55. A composition comprising the iron complex compound of any one of E24- and a pharmaceutically acceptable carrier.

E56. The iron complex compound of any one of E24-E54 or the composition of E55 for therapeutic use.

E57. The iron complex compound of any one of E24-E54 for use in treatment or prophylaxis of iron-deficiency in a subject.

E58. The iron complex compound for the use according to E57, wherein the subject is a non-human animal and the iron complex compound is selected from iron dextran, iron hydrogenated dextran and iron dextran glucoheptonic acid.

E59. The iron complex compound for the use according to E57, wherein the subject is a human suffering from lost or impaired kidney function, for example a human in need of dialysis.

E60. The iron complex compound for the use according to any one of E57-E59, wherein the subject is an infant.

E61. The iron material for the use according to E57 or E58, wherein the subject is a pregnant mammal or a mammal expected to become pregnant or a nursing mammal.

E62. The iron complex compound for the use according to any one of E57-E61, wherein the subject is selected from human, pig, horse, dog, cat, camel, sheep, goat and cow.

E63. The iron complex compound for the use according to any one of E57-E62, wherein the treatment or prophylaxis comprises parenteral administration of the iron complex compound.

E64. The iron complex compound for the use according to E63, wherein the parenteral administration is selected from intramuscular injection, subcutaneous injection, intravenous injection and intravenous infusion, and optionally is a bolus injection or infusion.

E65. The iron complex compound for the use according to any one of E57-E64, wherein the treatment or prophylaxis comprises the administration of a dose of the iron complex compound containing an amount of 200 mg or more iron within 2 minutes or less.

E66. The iron complex compound for the use according to any one of E57-E65, wherein the treatment or prophylaxis comprises the administration of one dose of iron complex compound containing an amount of 200 mg or more iron every four weeks or more frequently, for example every three weeks or more frequently, every three weeks or more frequently, or every week or more frequently.

E67. The iron complex compound for the use according to any one of E57-E66, wherein the treatment or prophylaxis comprises the administration of a single dose of iron complex compound containing an amount of 500 mg to 1000 mg iron.

E68. The iron complex compound for the use according to any one of E57-E66, wherein the treatment or prophylaxis comprises the administration of an amount of iron complex compound containing 15-20 mg iron per kg bodyweight of the subject in one sitting.

EXAMPLES

Example 1: Production of Ferric Chloride from Carbonyl Iron

Ferric Chloride was produced from carbonyl iron using a three step reaction in a nitrogen atmosphere.

Step 1: Carbonyl iron (5.2 kmol) was reacted with a slight excess of HCl (10.8 kmol) so as to form ferrous chloride and hydrogen.

The reaction in this step follows the equation:

$$Fe + 2HCl \rightarrow FeCl_2 + H_2$$

Step 2: The ferrous chloride obtained in step 1 was reacted with HCl (4.06 kmol) and a slight deficit of $NaClO_3$ (0.82 kmol) so as to form ferric chloride, sodium chloride and water.

The reaction in this step follows the equation:

$$6FeCl_2 + 6HCl + NaClO_3 \rightarrow 6FeCl_3 + NaCl + 3H_2O$$

Step 3: Residual ferrous chloride remaining after step 2 was converted to ferric chloride by controlled oxidation achieved by step-wise addition of hydrogen peroxide until no more ferrous iron was detected.

The main reaction in this step follows the equation:

$$FeCl_2 + 2HCl + H_2O_2 \rightarrow FeCl_3 + 2H_2O$$

There is a side reaction of hydrochloric acid and hydrogen peroxide following the equation:

$$2HCl + H_2O_2 \rightarrow Cl_2 + 2H_2O$$

Example 2: Production of Iron Complex Compounds from Carbonyl Iron

Iron isomaltoside 1000, an iron hydrogenated oligoisomaltose (oligoisomaltoside) complex compound, was produced using the process described in WO 2010/108493 A1.

$FeCl_3$ produced from carbonyl iron by the process described in example 1 was used. An amount of $FeCl_3$ containing 240 kg $Fe^{3+}$ was combined with 560 kg of a hydrogenated oligoisomaltose (oligoisomaltoside, i.e. isomaltoside 1000) preparation having a weight average molecular weight of 1,097 Da and a content of mono- and disaccharides of 0.8 wt-%. This produced 903 kg iron isomaltoside 1000 powder containing 24.2 wt-% $Fe^{3+}$. Thus about 91.1% $Fe^{3+}$ was incorporated into the final product that had the formula

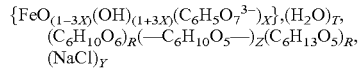

with X being about 0.031, T being about 0.25, R being about 0.14, Z being about 0.49 and Y being about 0.14.

Example 4: Non-Iron Metal Impurity Contents of Iron Complex Compounds

The amounts of non-iron metals in several iron complex compounds of the invention determined by ICP-MS are summarized in Table 1.

TABLE 1

| Non-iron metal impurity contents of iron complex compounds ||||||||
|---|---|---|---|---|---|---|---|
| Iron complex compound prepared from || Non-iron impurity content [µg per g iron] |||||| 
| Ligand | Iron preparation | Al | Cr | As | Cd | Hg | Pb |
| Low molecular weight dextran[#] | ferric chloride preparation according to example 1 | 9.7 | 1.4 | 0.1 | <0.001* | <0.02* | <0.003* |
| Low molecular weight dextran[#] | ferric chloride prepared by extracting an aqueous iron salt solution obtained during the processing of an iron-containing ore with an organic solvent | 9.3 | 19.5 | 0.2 | 0.1 | <0.02* | 0.1 |
| hydrogenated dextran[##] | ferric chloride prepared by extracting an aqueous iron salt solution obtained during the processing of an iron-containing ore with an organic solvent | 6.6 | 1.1 | 0.3 | 0.3 | <0.02* | 0.0 |
| iron isomaltoside 1000 according to example 2 || 6.3 | 10.7 | 1.2 | <0.001* | <0.02* | 0.2 |
| iron isomaltoside 1000 according to example 3 || 10.6 | 1.3 | 0.1 | 0.1 | <0.02* | 0.0 |

*limit of detection
[#]resulting iron dextran complex compound in accordance with British Pharmacopoeia monograph for Iron Dextran Injection
[##]weight average molecular weight (Mw) in the range of from 2,000 to 6,000 Da

Example 3: Production of Iron Complex Compounds from Ferric Chloride Derived by Extracting an Aqueous Iron Salt from an Aqueous Solution from Nickel Ore Using an Organic Solvent In a first step, a ferric chloride preparation was produced by providing an aqueous ferric chloride solution that was obtained during the processing of an iron-containing nickel ore for nickel production and extracting the aqueous ferric chloride solution using an organic solvent.

In a second step, iron isomaltoside 1000, an iron hydrogenated oligoisomaltoside complex compound, was produced using the process described in WO 2010/108493 A1.

An amount of the $FeCl_3$ obtained in the first step containing 240 kg $Fe^{3+}$ was combined with 560 kg of a hydrogenated oligoisomaltoside preparation having a weight average molecular weight of 1,022 Da and a content of mono- and disaccharides of 1.2 wt-%. This produced 888 kg iron hydrogenated oligoisomaltoside powder containing 24.8 wt-% $Fe^{3+}$. Thus about 91.8% $Fe^{3+}$ was incorporated into the final product that had the formula

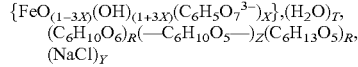

with X being about 0.031, T being about 0.25, R being about 0.14, Z being about 0.49 and Y being about 0.14.

The invention claimed is:

1. A process for preparing an iron complex compound comprising the steps of
   (i) obtaining an iron preparation from iron pentacarbonyl, wherein the iron preparation comprises iron in a form selected from a water-soluble iron salt, an iron hydroxide, an iron oxide-hydroxide and a mixture of two or more thereof, wherein
      the amount of arsenic in the iron preparation does not exceed 4.5 µg per g of iron, and
      the amount of lead in the iron preparation does not exceed 1.5 µg per g of iron;
   (ii) reacting the iron preparation with a ligand in the presence of water so as to form the iron complex compound,
   (iii) recovering said iron complex compound, and
   (iv) formulating said iron complex compound for parenteral administration.

2. The process of claim 1, wherein the amount of cadmium in the iron preparation does not exceed 0.6 µg per g of iron, and the amount of mercury in the iron preparation does not exceed 0.9 µg per g of iron.

3. The process of claim 1, wherein the amount of chromium in the iron preparation does not exceed 330 µg per g of iron.

4. The process of claim 1, wherein the amount of aluminum in the iron preparation does not exceed 200 µg per g of iron.

5. The process of claim 1, wherein the iron complex compound is an iron carbohydrate complex compound.

6. The process of claim 5, wherein the content of reducing aldehyde groups in the carbohydrate that serves as ligand in the iron complex compound has been reduced by oxidation, hydrogenation, or a combination of both.

7. The process of claim 5, wherein the iron carbohydrate complex compound is selected from iron carboxymaltose, iron polyglucose sorbitol carboxymethyl ether complex, iron hydrogenated dextran, iron sucrose, iron gluconate, iron polymaltose, iron dextran, iron hydrogenated oligosaccharides, iron hydroxyethyl starch, iron dextran glucoheptonic acid and a mixture of two or more thereof.

8. The process of claim 7, wherein said iron hydrogenated oligosaccharides comprise iron hydrogenated oligoisomaltose.

9. The process of claim 1, wherein step (ii) comprises heating said iron preparation and ligand in the presence of water to boiling.

10. The process of claim 1, wherein in step (iv) said iron complex compound is formulated for administration to a non-human animal.

11. The process of claim 1, wherein in step (iv) said formulation is for subcutaneous injection, intramuscular injection, intravenous injection, or intravenous infusion.

12. A process for preparing an iron complex compound comprising the steps of
  (i) obtaining an iron preparation by extracting an aqueous iron salt solution with an organic solvent, wherein the iron preparation comprises iron in a form selected from a water-soluble iron salt, an iron hydroxide, an iron oxide-hydroxide and a mixture of two or more thereof, wherein
    the amount of arsenic in the iron preparation does not exceed 4.5 µg per g of iron, and
    the amount of lead in the iron preparation does not exceed 1.5 µg per g of iron;
  (ii) reacting the iron preparation with a ligand in the presence of water so as to form the iron complex compound, and
  (iii) recovering said iron complex compound.

13. The process of claim 12, further comprising formulating said iron complex compound for administration.

14. The process of claim 13, wherein said formulation is for parenteral administration, subcutaneous injection, intramuscular injection, intravenous injection, or intravenous infusion.

15. The process of claim 12, wherein the amount of cadmium in the iron preparation does not exceed 0.6 µg per g of iron, and the amount of mercury in the iron preparation does not exceed 0.9 µg per g of iron.

16. The process of claim 12, wherein the amount of chromium in the iron preparation does not exceed 330 µg per g of iron.

17. The process of claim 12, wherein the amount of aluminum in the iron preparation does not exceed 200 µg per g of iron.

18. The process of claim 12, wherein the iron complex compound is an iron carbohydrate complex compound.

19. The process of claim 18, wherein the content of reducing aldehyde groups in the carbohydrate that serves as ligand in the iron complex compound has been reduced by oxidation, hydrogenation, or a combination of both.

20. The process of claim 18, wherein the iron carbohydrate complex compound is selected from iron carboxymaltose, iron polyglucose sorbitol carboxymethyl ether complex, iron hydrogenated dextran, iron sucrose, iron gluconate, iron polymaltose, iron dextran, iron hydrogenated oligosaccharides, iron hydroxyethyl starch, iron dextran glucoheptonic acid and a mixture of two or more thereof.

21. The process of claim 20, wherein said iron hydrogenated oligosaccharides comprise iron hydrogenated oligoisomaltose or iron hydrogenated dextran.

22. The process of claim 21, wherein the carbohydrate component of said iron hydrogenated oligoisomaltose or iron hydrogenated dextran has a weight average molecular weight ($M_W$) of between 500 to 80,000 Da.

23. The process of claim 21, wherein the apparent molecular weight of said iron hydrogenated oligoisomaltose is between 20,000 to 400,000 Da.

24. The process of claim 21, wherein said iron hydrogenated oligoisomaltose has the formula:

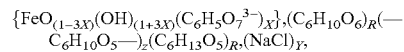

wherein X is about 0.031, T is about 0.25, R is about 0.14, Z is about 0.49, and Y is about 0.14.

25. The process of claim 12, wherein step (ii) comprises heating said iron preparation and ligand in the presence of water to boiling.

* * * * *